United States Patent [19]
Mann

[11] Patent Number: 5,514,081
[45] Date of Patent: *May 7, 1996

[54] ELBOW ORTHOSIS HAVING AN INFLATABLE BLADDER SUPPORT AND METHOD OF USE

[75] Inventor: Donaerl B. Mann, Ft. White, Fla.

[*] Notice: The portion of the term of this patent shall not extend beyond the expiration date of Pat. No. 5,462,517.

[73] Assignee: D'Mannco, Inc., High Springs, Fla.

[21] Appl. No.: 319,597

[22] Filed: Oct. 7, 1994

[51] Int. Cl.⁶ ........................................... A61F 5/00
[52] U.S. Cl. ..................... 602/20; 602/13; 128/DIG. 20
[58] Field of Search .................................. 602/5, 13, 12, 602/16, 20, 22, 23, 62, 64, 26, 21; 128/DIG. 20

[56] References Cited

U.S. PATENT DOCUMENTS

| | | |
|---|---|---|
| 3,548,820 | 12/1970 | Bergen . |
| 3,993,056 | 11/1976 | Rabischong . |
| 4,340,042 | 7/1982 | Smith . |
| 4,873,968 | 10/1989 | Finnieston et al. ............... 602/21 |
| 4,938,207 | 7/1990 | Vargo . |
| 4,947,834 | 8/1990 | Kartheus . |
| 4,960,115 | 10/1990 | Ranciato . |
| 5,056,504 | 10/1991 | Mann . |
| 5,205,812 | 4/1993 | Wasserman ................. 602/21 X |
| 5,378,224 | 1/1995 | Bilotti ............................. 602/13 |

Primary Examiner—Richard J. Apley
Assistant Examiner—Beverly M. Flanagan
Attorney, Agent, or Firm—Herbert W. Larson

[57] ABSTRACT

A cloth body having a central elbow portion wrapped around a patient's elbow to treat elbow flexion contractures. Hook and loop material secure the cloth body to the patient's elbow. A longitudinally extending pocket contains an air bladder. Inflation of the air bladder supports the patient's elbow in a rigid position. Latitudinally extending pockets surrounding the anterior portion of the forearm and upper arm contain a flexible support element.

9 Claims, 6 Drawing Sheets

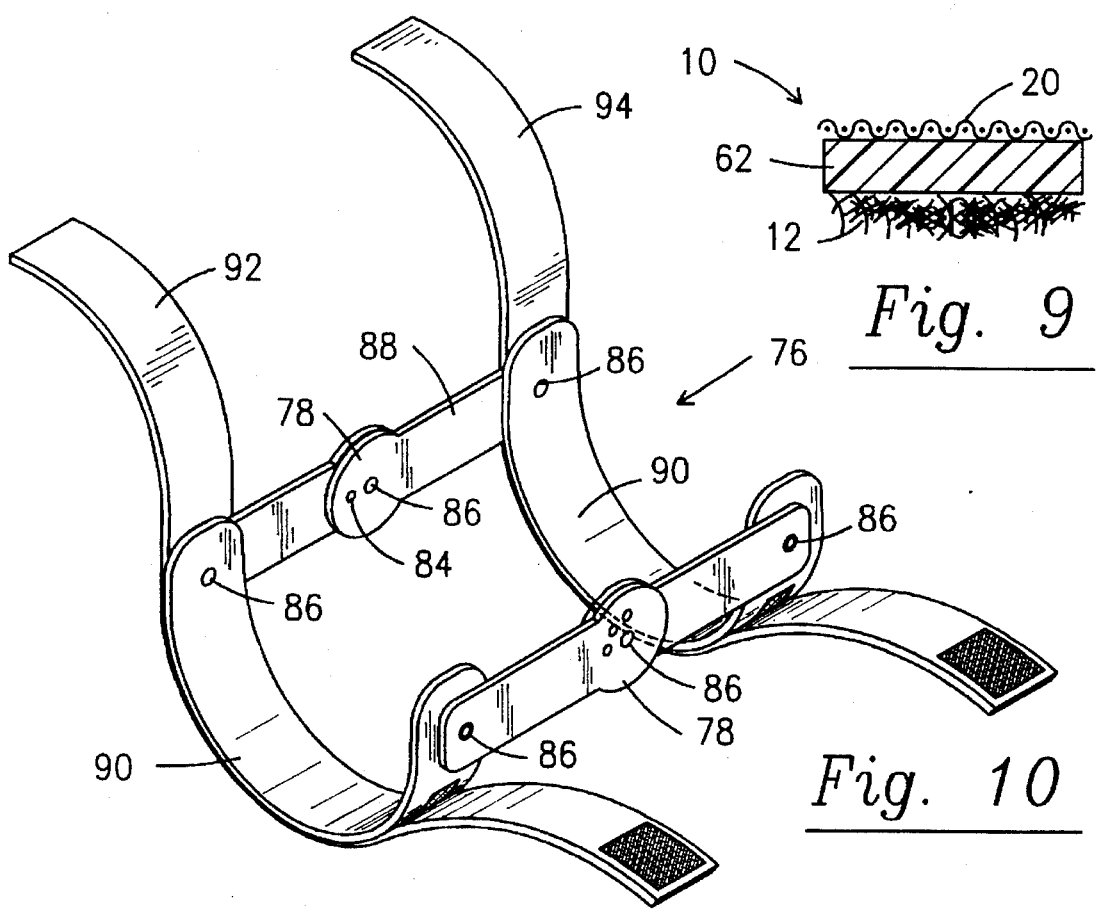
Fig. 9
Fig. 10
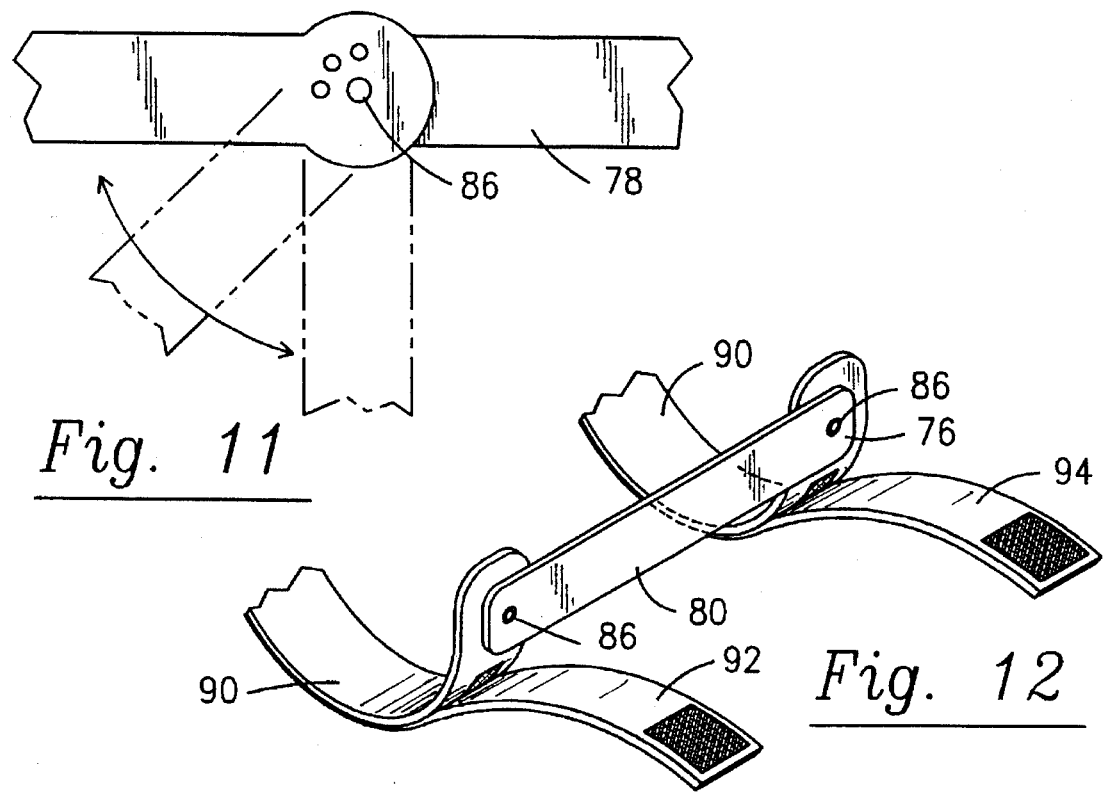
Fig. 11
Fig. 12

ELBOW ORTHOSIS HAVING AN INFLATABLE BLADDER SUPPORT AND METHOD OF USE

PRIOR APPLICATIONS

This application is related to application Ser. No. 08/294086, filed Aug. 22, 1994, which is a continuation-in-part of application Ser. No. 07/904,844, filed on Jun. 26, 1992.

BACKGROUND OF THE INVENTION

1. Field of the Invention

This invention relates to orthopedic elbow brace appliances. More particularly it refers to an orthopedic appliance applied to a patient's elbow, the appliance containing an air bladder inflated to extend a contracted elbow in a rigid configuration.

2. Description of Prior Art

Many orthopedic appliances exist containing air bladders or fluid control chambers for intermittently supporting and releasing support on body parts. U.S. Pat. No. 3,993,056 describes such appliances having inflatable tubes stitched into a fabric extending vertically over a portion of the fabric. U.S. Pat. No. 4,430,042 describes a pillow type device strapped to a leg and then inflated. U.S. Pat. No. 4,872,448 describes a U-shaped inflatable air bladder over the patella. U.S. Pat. No. 4,938,207 describes a linear brace employing first and second fluid filled chambers. U.S. Pat. No. 4,947,834 describes a brace for compressing a patient's outer extremities, the brace having flexible chambers arranged one after another in a series and these are successively inflated. U.S. Pat. No. 4,960,115 describes a body support apparatus having at least two inflation chambers. U.S. Pat. Nos. 5,020,515 and 5,056,504 describe hand splints with inflatable bladders.

None of these appliances provides a means to alternately support a patient's elbow in various positions and permit easy removal and reapplication of the splint for treating wounds under the brace. A need exists to have flexibility in an elbow brace support appliance for treating elbow flexion contractures and to obtain ease of removing and reapplying the brace.

SUMMARY OF THE INVENTION

I have invented an elbow brace having an inflatable bladder support to treat elbow flexion contractures. My elbow brace has a cloth body having a soft bottom portion in contact with the patient's skin and a fabric top surface to which a longitudinal pocket is attached, the longitudinal pocket containing a plastic air bladder. A pair of latitudinal pockets are located at right angles to the air bladder and each contains a rigid support element. In a preferred embodiment, the latitudinal pockets are sealed and contain a moldable plastic conforming with a patient's anterior portion of the forearm and upper arm. Hook or loop closures are attached to the top surface of the brace and corresponding bottom surface of the brace to hold the elbow brace in place around the patient's elbow. A hand pump is attached to the bladder to inflate or deflate the bladder as needed by the patient. The wrap around fastening of the cloth body allows for treatment of wounds and incisions by unfastening the hook and loop closures, treating the wound, and easily reapplying the brace.

In an alternate embodiment, an exoskeleton frame is provided for surrounding the cloth body and providing a means to set the elbow in a multiplicity of fixed positions. The exoskeleton frame is secured to the cloth body by straps having hook and loop material surrounding the outer surface of the cloth body.

BRIEF DESCRIPTION OF THE DRAWINGS

The invention may be best understood by those having ordinary skill in the art by reference to the following detailed description when considered in conjunction with the accompanying drawings in which:

FIG. 9 is a cross sectional view through the cloth body of the orthopedic appliance shown in FIG. 1.

FIG. 10 is a perspective view of an exoskeleton frame having a hinged support portion for use with the orthopedic appliance of my invention.

FIG. 11 is a side view in partial phantom of a portion the exoskeleton frame illustrating the different positions in which the hinged support portion can be set.

FIG. 12 is a partial perspective view of an exoskeleton frame having a rigid support portion for use with the orthopedic appliance of my invention.

DETAILED DESCRIPTION OF THE INVENTION

Figure 1:
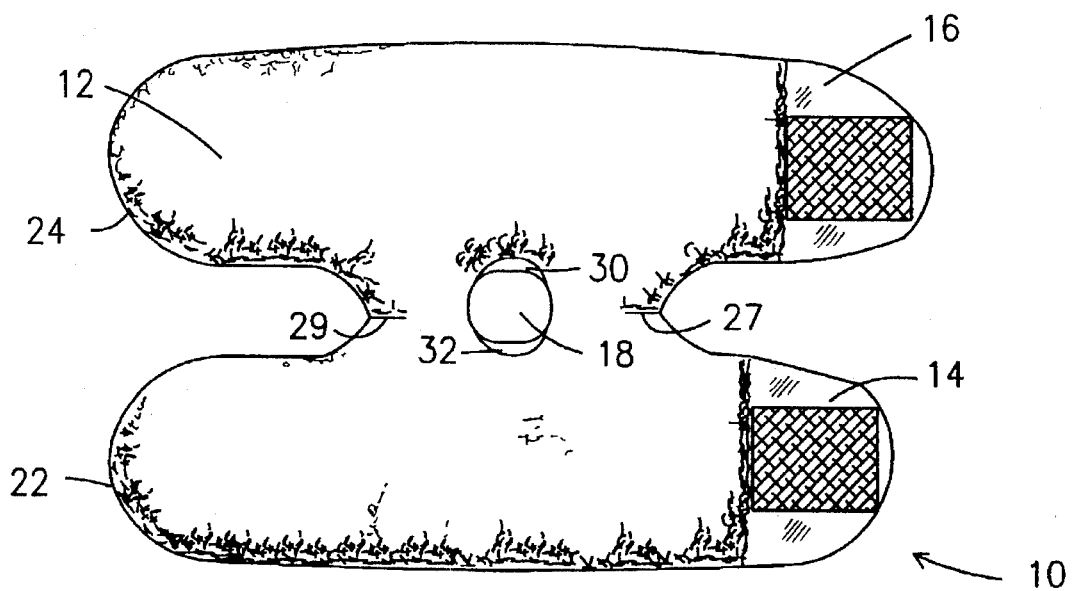
FIG. 1 is a bottom plan view of the orthopedic appliance of my invention prior to applying the appliance to a patient.

Throughout the following detailed description, the same reference numerals refer to the same elements in all figures.

The elbow brace or orthosis appliance 10 is shown in FIG. 1 presenting a bottom plan view thereof. The bottom portion is covered by a pile 12 such as KODEL, a registered trademark for a product sold by Eastman Kodak Company, or other soft wool or wool like material which will not be abrasive to a patient's skin surface. A section 14 and 16 projecting from the pile 12 contain hook or loop material used in fastening the brace 10 to a patient's elbow. A hole 18 in the pile 12 approximately centrally located in the pile material 12 accepts the anterior elbow joint.

Figure 2:
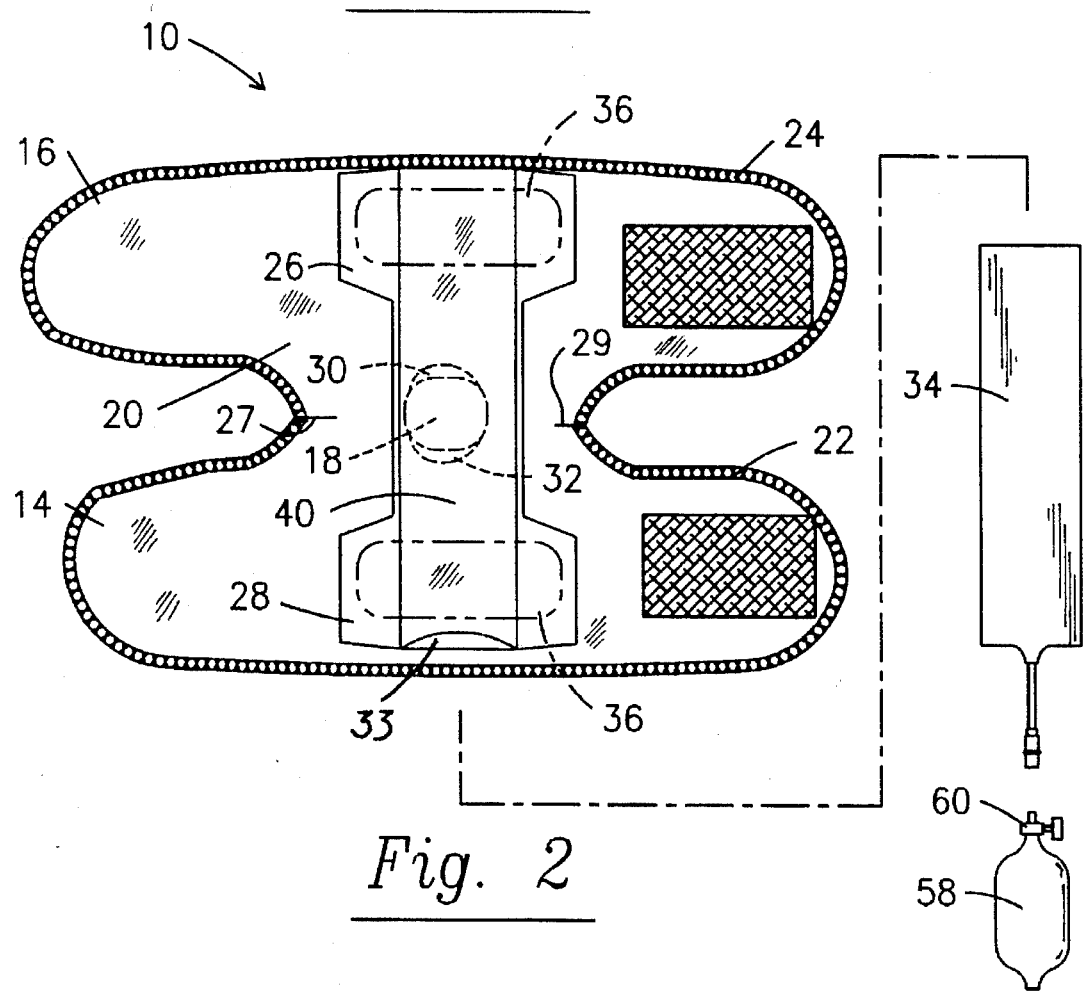
FIG. 2 is a top plan view of the orthopedic appliance shown in FIG. 1.
Figure 4:
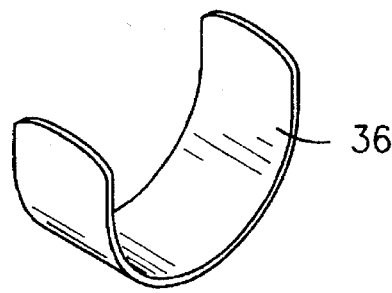
FIG. 4 is a perspective view of the support element in its position around a forearm or upper arm and molded to the shape of the anterior portion of a patient's forearm and upper arm.
Figure 5:
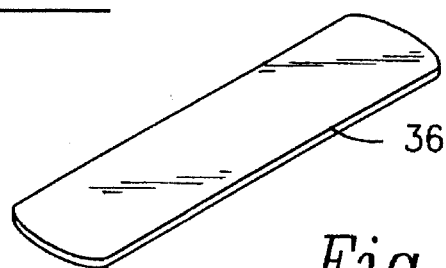
FIG. 5 is a perspective view of a rigid support element before deployment around a patient's arm.
Figure 6:
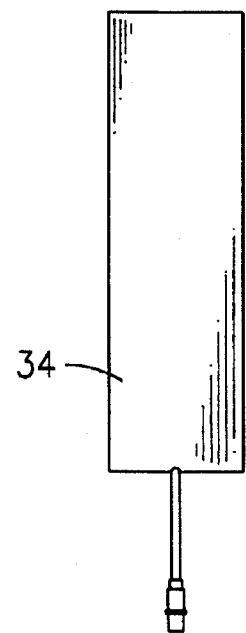
FIG. 6 is a top plan view of the air bladder which inserts within a pocket.

FIG. 2 shows a top plan view of the elbow brace 10. The top surface of the brace is covered by tightly woven fabric 20. A pair of projecting sections 22 and 24, oppositely positioned sections 14 and 16 respectively, have hook and loop material attached by sewing to the tightly woven fabric 20. As shown in FIG. 1, the bottom portions of sections 22 and 24 are covered by the pile 12. Also shown in FIG. 2 is a pair of latitudinal pockets 26 and 28 respectively sewn to the top surface of the fabric 20. An opening 30 to pocket 26 and an opening 32 to pocket 28 provides a means for inserting a rigid support element 36 such as polyethylene into each pocket. The support elements 36 are inserted into openings 30 and 32 from the bottom surface of elbow brace 10 as shown in FIG. 1. Another pocket 40 longitudinally positioned has an opening 33 for insertion of a bladder 34. The rigid support elements 36, as shown respectively in FIGS. 4 and 5, are insertable into pockets 26 and 28 in either a curved position as shown in FIG. 4 or inserted as shown in FIG. 5 and then molded to the patient's forearm or upper arm. Darts 27 and 29 on fabric 20 enhance the ability to fold the brace 10 together and conforming the elbow brace 10 to the curve of the patient's arm.

Figure 3:
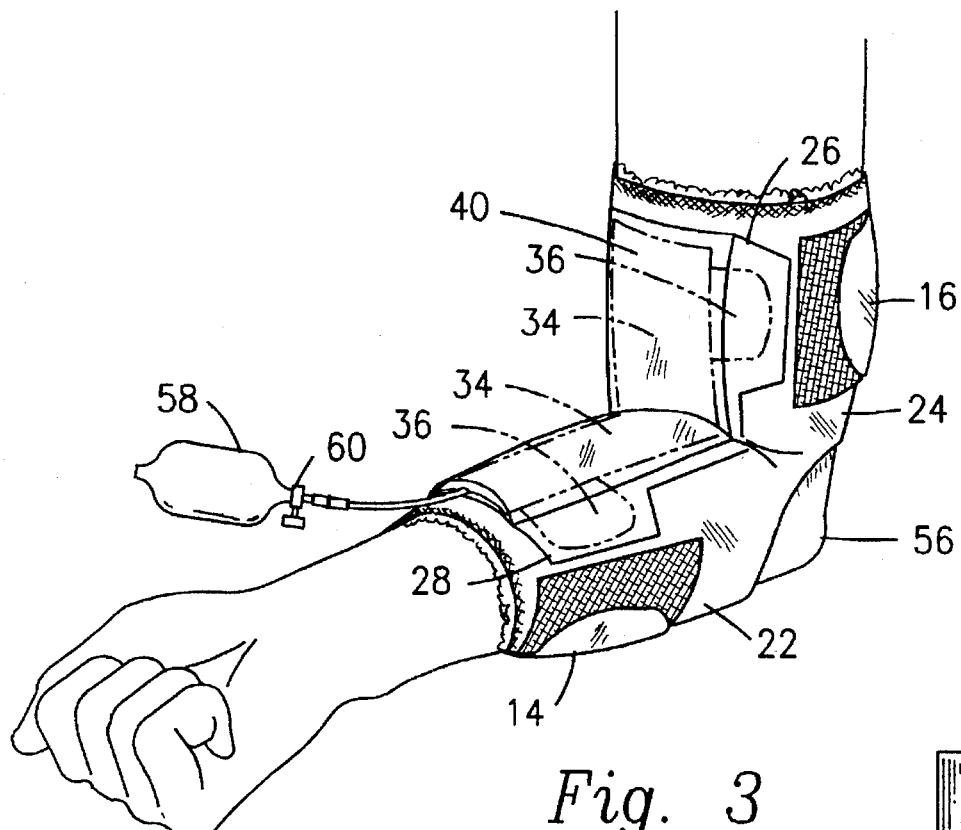
FIG. 3 is a perspective view of the orthopedic appliance shown in FIG. 1, positioned on a patient's elbow with an air bladder and pair of support elements shown in phantom.

FIG. 3 shows the brace 10 mounted over the elbow 56 of a patient. Section 16 is folded over on to section 24 so that the hook or loop material on the bottom of section 16 engages the corresponding hook or loop material on the top of section 24. In like manner, the section 14 is passed over section 22 so that the hook or loop material on the bottom portion of section 14 engages the corresponding hook or loop material on the top portion of section 22. In the brace 10, shown in FIG. 3, support element 36 is employed in the pocket 26. Bladder 34 is shown in the deflated position so that the patient can bend his or her arm. A bulb pump 58 is attached by its valve 60 to the corresponding valve opening in bladder 34 to enable the bladder to be expanded and straighten the patient's elbow in the designated position.

Figure 7:
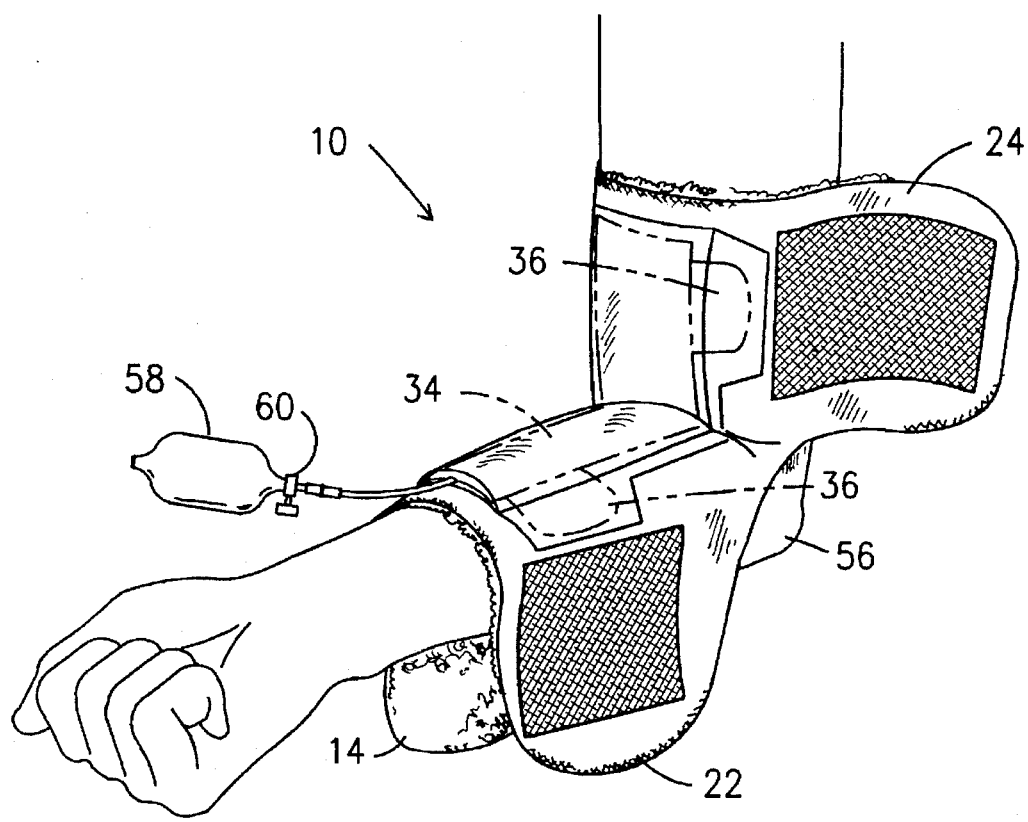
FIG. 7 is a perspective view of the orthopedic appliance shown in FIG. 1, draped over a patient's elbow with the air bladder and support elements shown in phantom.
Figure 8:
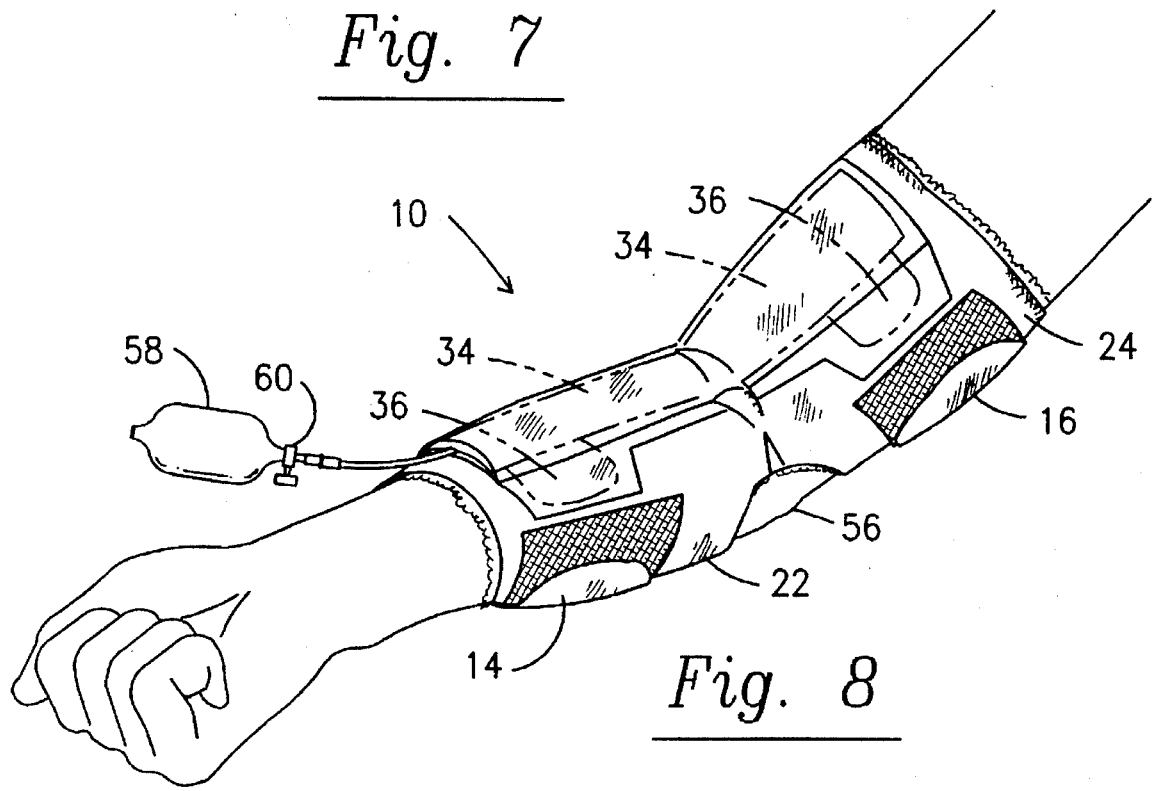
FIG. 8 is a perspective view of the orthopedic appliance shown in FIG. 1, retaining a patient's elbow in a fixed extended position.

As shown in FIG. 7, the rigid support elements 36 are employed in the pockets. The inflated bladder 34 maintains a completely rigid configuration for the patient's elbow.

As shown in FIG. 9, the top surface of tightly woven fabric 20 is separated from the bottom portion covered by a pile 12 by an intermediate foam layer 62 so that the brace 10 has a soft wool-like material 12 in contact with the skin and a durable fabric 20 on the outside protecting the brace 10 from environmental effects, but with a foam intermediate material to maintain the body structure of the brace 10 while at the same time providing a soft medium 12 to prevent pressure against the soft tissue of the arm.

The elbow brace 10 of this invention is designed primarily to treat pre-fixed contracture of the elbow. Such pre-fixed contracture is any contracted joint that can be flexed or extended and where splinting is indicated for treatment. The brace 10 will stabilize the extension of the elbow and is useful for immobilization of the elbow during post-trauma or post-surgery. In addition, the brace 10 will support post-trauma or surgery patients while undergoing rehabilitation.

In placing the brace 10 on a patient, the elbow can be extended as far as comfort will allow and the open brace 10 is placed on the patient's elbow with the section 16 placed around the forearm to contact the section 24 on the fabric, and the section 14 placed around the upper arm to contact the section 22 on the fabric. The pile surface 12 is placed down over the patient's skin. The air bladder is inflated to hold the elbow in the degree of extension desired. The greater the degree of extension, the more inflation in the air bladder 34. Once the amount of air pressure necessary for either stabilization or immobilization has been determined, the brace 10 can be removed and put back on without changing the air pressure in the air bladder 34. To remove the brace 10 the hook and loop material is unfastened. To replace the brace 10, extend the arm and place the brace 10 pile side 12 toward and under the elbow 56 and fasten the hook and loop ends together. One finger should be inserted under all edges for correct clearance. The brace 10 can be easily removed and replaced in order to treat wounds under the splinted area.

Figure 13:
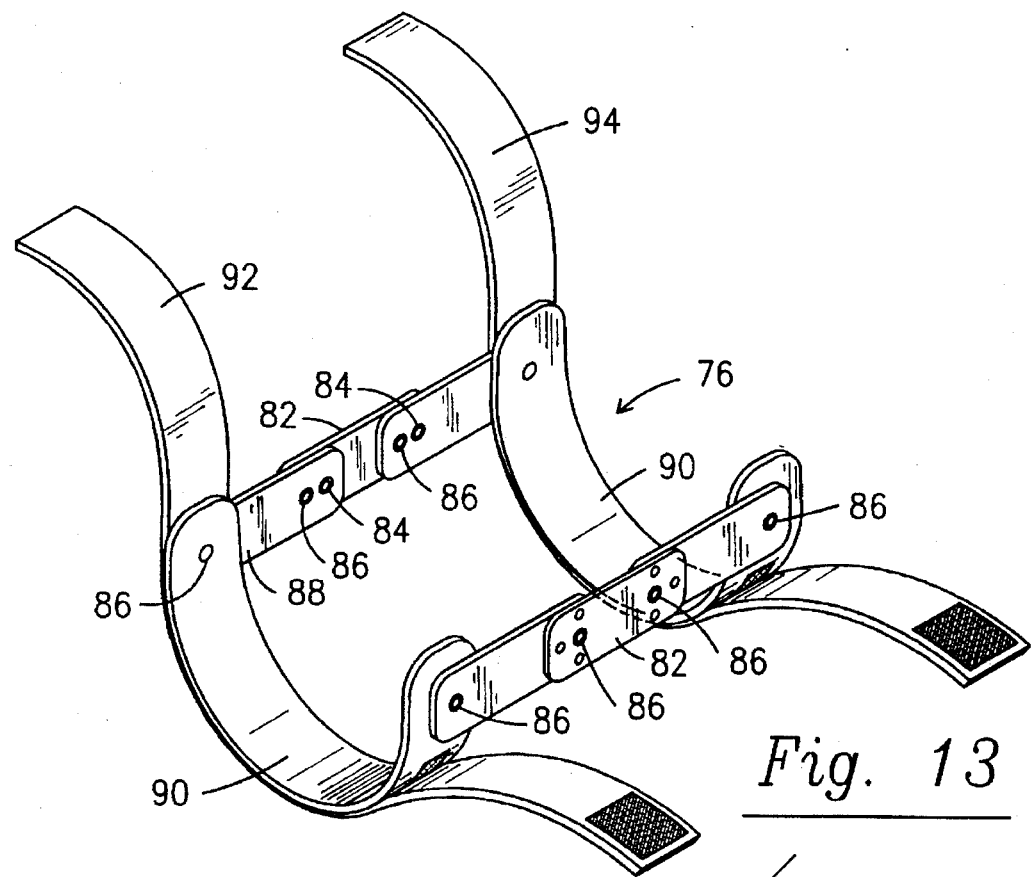
FIG. 13 is a perspective view of an exoskeleton frame having a polycentric support portion for use with the orthopedic appliance of my invention.
Figure 14:
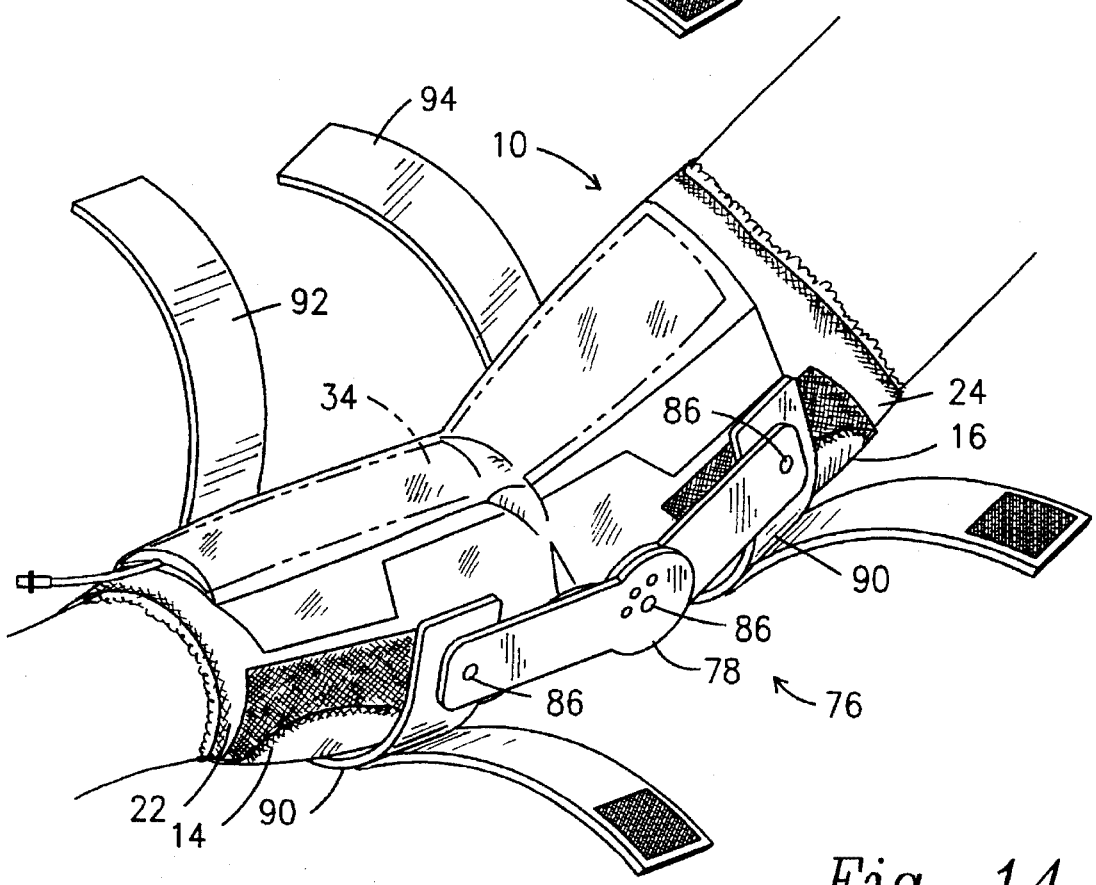
FIG. 14 is a perspective view of the orthopedic appliance of FIG. 2 with the exoskeleton frame draped over a patient's elbow, the exoskeleton frame having a hinged support portion.
Figure 15:
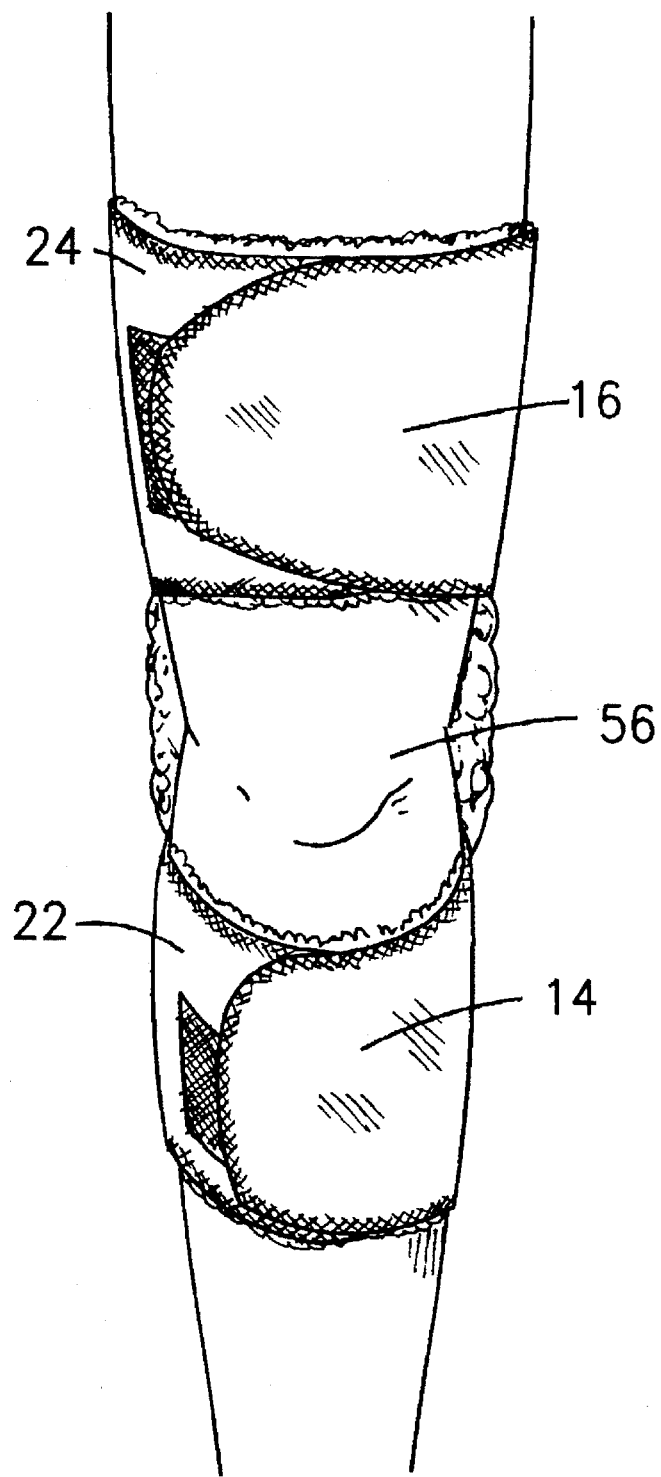
FIG. 15 is an anterior view of a patient's elbow with the orthopedic appliance retaining the elbow in a fixed position.

Referring to FIGS. 10, 12 and 13, an exoskeleton frame 76 is provided for use with brace 10. Exoskeleton frame 76 can be positioned around brace 10 in conjunction with the rigid support elements 36. FIG. 14 shows exoskeleton frame 76 employed around brace 10.

Exoskeleton frame 76 is provided with a plurality of interchangeable support portions for setting an elbow of a patient in a variety of fixed positions. FIG. 10 shows exoskeleton frame 76 having a preferred hinged support portion 78. FIG. 11 illustrates the variety of fixed positions in which hinged support portion 78 of exoskeleton frame 76 can be set. FIG. 12 shows exoskeleton frame 76 having a rigid support portion 80. FIG. 13 shows exoskeleton frame 76 having a polycentric support portion 82. Polycentric support portion 82 allows exoskeleton frame 76 to be locked in a variety of fixed positions as shown in FIGS. 13 and 14. Hinged support portion 78 and polycentric support portion 82 are locked in their respective fixed position by a preferred push button mechanism 84, although removable screws (not shown) could be employed to achieve the same result. The push button mechanism 84 is engagable from an inner surface 88 along hinged support portion 78 and polycentric support portion 82, as shown in FIGS. 10 and 13 respectively. A plurality of Chicago screws 86 permit rotation of hinged support portion 78 and polycentric support portion 82. As shown in FIGS. 10, 12, and 13, a pair of flexible support portions 90 are provided with exoskeleton frame 76 to provide medial support to the tendons along the dorsal portion of the forearm and upper arm. Flexible support portions 90 are rotatably attached to either hinged, rigid, or polycentric support portions 78, 80, and 82 respectively, by Chicago screws 86.

Straps 92 and 94 containing hoop and loop material are wrapped around the frame 76 to keep it in place. The elbow brace or orthosis appliance 10 has its air bladder 36 lying on the supinated portion of the arm. It is centered over the inner, anterior aspect of the elbow joint.

A pocket 40 in the middle, outside of the orthosis 10 holds the inflatable air bladder 34 in place. The pair of malleable rigid stays 36 are incorporated onto the soft cover beneath the bladder pocket. The stays are formed to fit the curve of the upper and lower arm and are designed to disperse the pressure from the upper and lower muscle mass to the sides of the arm.

The air bladder 34 is slowly inflated to increase the pressure against the upper and lower arm. This will hold the contracted arm in the extended range of motion position. The inflatable air bladder 34 maintains the arm in an extended position without undo pressure on the flexors above and below the elbow joint. The air bladder 34 allows continuous motion of the elbow joint by resisting the flexion contractors with resultant relation of the flexor muscles. There is minimal pressure against the soft tissue and the orthosis 10 does not constrict the blood flow nor cause pressure on the nerves.

With daily range of motion therapy and careful use of the elbow orthosis 10, flexion contractors can be effectively treated. When used as a resting brace at night, the elbow brace will prevent flexion contracture in early immobility and treat long standing non-fixed contractores.

The elbow orthosis 10 is easy to apply and the materials used, encourage patient compliance.

The plastic employed in the support element 36 can be a moldable low density polyethylene which has a memory and will return to a shallow curve but will not return to the previous straight configuration. By using such a polyethylene the pressure from the air bladder is diverted to the edges of the rigid support elements 36 and causes a pull against the backs of the upper and lower arm. At the same time it does not put pressure on the anterior reflex muscles.

Equivalent materials can be substituted for the materials employed in this invention to obtain substantially the same result in the same way.

Having thus described the invention what is claimed and desired to be secured by Letters Patent is:

1. An orthopedic appliance for surrounding an elbow of a patient to treat elbow flexion contractures, the appliance comprising, a cloth body having a top and bottom layer, a foam layer located intermediate the top and bottom layers, and a generally centrally located portion for receiving a patient's elbow, the top layer covered by a tightly woven fabric, the bottom layer covered by a soft non-abrasive material for contact with the skin of the patient, the cloth body wrapped around the elbow of the patient such that an area is provided from which an anterior portion of the elbow can protrude through at least the bottom and foam layer of the cloth body, hook or loop material attached to a top and bottom portion of the top layer of the cloth body at opposed ends for securing the cloth body in a wrapped position, a longitudinal pocket integrally attached to the top layer of the cloth body, the longitudinal pocket having an opening formed therein, an air bladder mounted within the longitudinal pocket, the air bladder permitting inflation to set the elbow in a desired position and deflation so that the patient can flex the elbow, the air bladder having been inserted through the opening in the longitudinal pocket, and two latitudinal pockets at right angles to the air bladder, a support element mounted within each latitudinal pocket for providing support to the orthopedic appliance.

2. The orthopedic appliance according to claim 1 wherein each latitudinal pocket has an opening at opposed sides of the area of the cloth body in which the anterior portion of the elbow protrudes and the latitudinal support elements have been mounted within the latitudinal pockets through the openings.

3. The orthopedic appliance according to claim 2 wherein the latitudinal support element is a flat structure made from a moldable low density polyethylene.

4. The orthopedic appliance according to claim 2 wherein the latitudinal support elements are a first curved structure conforming to an anterior portion of the patient's upper arm and a second curved structure conforming to an anterior portion of the patient's forearm.

5. An orthopedic appliance for surrounding an elbow of a patient to treat elbow flexion contractures, the appliance comprising, a cloth body having a top and bottom layer, a foam layer located intermediate the top and bottom layers, and a generally centrally located portion for receiving a patient's elbow, the top layer covered by a tightly woven fabric, the bottom layer covered by a soft non-abrasive material for contact with the skin of the patient, the cloth body wrapped around the elbow of the patient, hook or loop material attached to the top layer of the cloth body at opposed ends for securing the cloth body in a wrapped position, a longitudinal pocket integrally attached to the top layer of the cloth body, the longitudinal pocket having an opening formed therein, an air bladder mounted within the longitudinal pocket, the air bladder adapted to be inflated from an air pump to rigidly set the elbow in a desired position and deflation so that the patient can flex the elbow, the air bladder having been inserted through the opening in the longitudinal pocket, and an exoskeleton frame surrounding the cloth body and having a pair of stiff support portions rotatably attached to a pair of flexible support portions at opposed ends of the stiff and flexible support portions respectively, the pair of the flexible support portions for surrounding an anterior portion of a forearm and upper arm of the patient, the stiff support portions for positioning along opposed sides of the elbow adjacent the air bladder, the flexible support portions having an outer surface for attaching a pair of hook and loop straps by hook and loop material, and the hook and loop straps securing the exoskeleton frame around the cloth body of the orthopedic appliance.

6. The orthopedic appliance for surrounding an elbow of a patient to treat elbow flexion contractures according to claim 5, wherein the pair of stiff support portions are hinged to permit the patient's elbow to be set in a variety of fixed positions.

7. The orthopedic appliance for surrounding an elbow of a patient to treat elbow flexion contractures according to claim 5, wherein the pair of stiff support portions are rigid to restrict movement of the elbow, the support portions setting the elbow in a straight and fixed position.

8. The orthopedic appliance for surrounding an elbow of a patient to treat elbow flexion contractures according to claim 5, wherein the pair of stiff support portions are polycentric to permit movement of the elbow and to allow the elbow to be set in a variety of fixed positions.

9. A method of moving a contracted arm of a patient to a more extended position comprising:

wrapping a forearm and upper arm of the patient in a cloth body having multiple layers with hook or loop material attached to a top and bottom portion of the cloth body at opposed ends for securing the cloth body in a wrapped position, inserting an air bladder into a longitudinal pocket in the cloth body, inserting a rigid support element into one or more latitudinal pockets in the cloth body, inserting a stem leading to a hand held air pump into the air bladder and alternating inflating and deflating the air bladder to exercise the patient's contracted arm.

* * * * *